(12) United States Patent
Manstein

(10) Patent No.: US 10,092,354 B2
(45) Date of Patent: Oct. 9, 2018

(54) METHOD AND APPARATUS FOR SKIN STABILIZATION AND POSITIONING

(71) Applicant: The General Hospital Corporation, Boston, MA (US)

(72) Inventor: Dieter Manstein, Miami, FL (US)

(73) Assignee: The General Hospital Corporation, Boston, MA (US)

( * ) Notice: Subject to any disclaimer, the term of this patent is extended or adjusted under 35 U.S.C. 154(b) by 860 days.

(21) Appl. No.: 14/461,203

(22) Filed: Aug. 15, 2014

(65) Prior Publication Data

US 2014/0358133 A1 Dec. 4, 2014

Related U.S. Application Data

(63) Continuation of application No. 12/910,646, filed on Oct. 22, 2010, now abandoned.
(Continued)

(51) Int. Cl.
*A61B 18/20* (2006.01)
*A61B 18/22* (2006.01)
(Continued)

(52) U.S. Cl.
CPC .............. *A61B 18/20* (2013.01); *A61B 18/22* (2013.01); *A61M 37/00* (2013.01); *A61B 18/203* (2013.01); *A61B 2018/0047* (2013.01); *A61B 2018/00452* (2013.01); *A61B 2018/00458* (2013.01); *A61B 2018/00577* (2013.01); *A61B 2018/2005* (2013.01); *A61H 39/02* (2013.01); *A61M 2037/0007* (2013.01)

(58) Field of Classification Search
CPC ....... A61B 18/20; A61B 18/203; A61B 18/22; A61B 2018/00452; A61B 2018/00458
See application file for complete search history.

(56) References Cited

U.S. PATENT DOCUMENTS 5,116,324 A 5/1992 Brierley et al.
5,879,373 A 3/1999 Roper et al.
(Continued)

FOREIGN PATENT DOCUMENTS

EP 1752086 A2 2/2007
WO WO 00/76575 12/2000
WO WO 2004/086947 A2 10/2014

OTHER PUBLICATIONS

European Office Action for Application No. 10825781.7 dated Jun. 26, 2015.
Fourth Office Action for Chinese Application No. 201080054476.3 dated Sep. 6, 2015.
First Office Action and the Examination Search Report for Canadian Application No. 2,779,300 dated Aug. 26, 2016.
(Continued)

*Primary Examiner* — Diane Yabut
(74) *Attorney, Agent, or Firm* — Hunton Andrews Kurth LLP

(57) ABSTRACT

Exemplary embodiments of a method, device, and apparatus for positioning an apparatus on a location of a tissue. For example, a substantially rigid film over an area of tissue to be treated can be provided. The film can include a positioning arrangement that facilitates a particular spatial engagement with the apparatus. The exemplary method can further include applying a portion of the film to a portion of a surface of the tissue and positioning the apparatus at the location by the engagement of the film to the apparatus using the feature of the film.

15 Claims, 5 Drawing Sheets

Related U.S. Application Data

(60) Provisional application No. 61/254,061, filed on Oct. 22, 2009.

(51) Int. Cl.
*A61M 37/00* (2006.01)
*A61H 39/02* (2006.01)
*A61B 18/00* (2006.01)

(56) References Cited

U.S. PATENT DOCUMENTS

| | | |
|---|---|---|
| 6,412,491 B1 | 7/2002 | Rusin |
| 6,685,699 B1 * | 2/2004 | Eppstein ............... A61B 18/203 606/13 |
| 6,743,211 B1 | 6/2004 | Prausnitz et al. |
| 6,925,317 B1 * | 8/2005 | Samuels ............ A61B 5/14514 600/309 |
| 2002/1693945 | 11/2002 | Eppstein et al. |
| 2003/0005938 A1 | 1/2003 | Lockwood |
| 2005/0014997 A1 | 1/2005 | Ruchti et al. |
| 2005/0222565 A1 | 10/2005 | Manstein |
| 2007/0068537 A1 | 3/2007 | Giovannoli |
| 2007/0239236 A1 | 10/2007 | Manstein |
| 2008/0082090 A1 | 4/2008 | Manstein |
| 2009/0048563 A1 | 2/2009 | Ethelfeld et al. |
| 2009/0062781 A1 | 3/2009 | Wolfgang Strasser et al. |

OTHER PUBLICATIONS

Communication Pursuant to Article 94(3) EPC dated Jan. 31, 2017 for European Patent Application No. 10825781.7.
Communication Pursuant to Article 94(3) EPC dated Apr. 10, 2014 for European Patent Application No. 10825781.7.
Notification of the First Office Action dated Dec. 3, 2013 for Chinese National Phase application No. 201080054476.3.
Notification of the Second Office Action dated Aug. 26, 2014 for Chinese National Phase Application No. 201080054476.3.
Notification for Patent Registration Formalities dated Mar. 7, 2016 for Chinese National Phase Application No. 201080054476.3.
Notice Before Acceptance dated Jan. 31, 2016 for Israeli National Phase Application No. 219300.
Third Office Action for Chinese Application No. 201080054476.3 dated Mar. 9, 2015.
First Office Action for Israeli Patent Application No. 219300 dated Nov. 11, 2014.
International Search Report dated Jul. 26, 2011 for PCT/US2010/053840.
European Search Report for Europeant Patent Application No. 10825781.7 dated Mar. 13, 2013.
Second Office Action and the Supplemental Search Report for Chinese Patent Application No. 201080054476.3 dated Aug. 26, 2014.

* cited by examiner

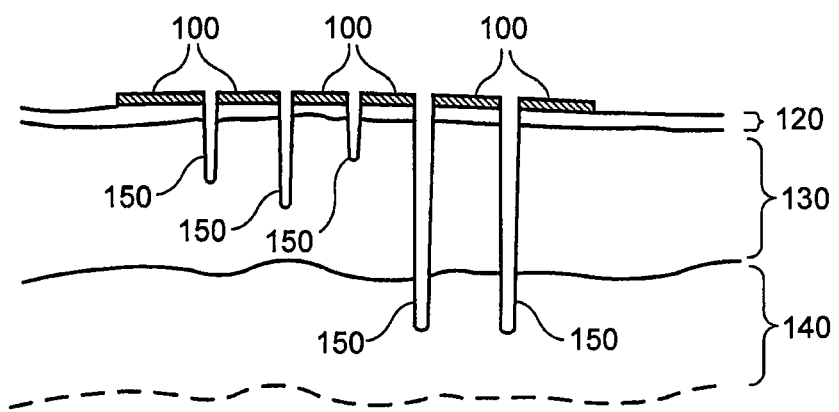
F I G. 1A
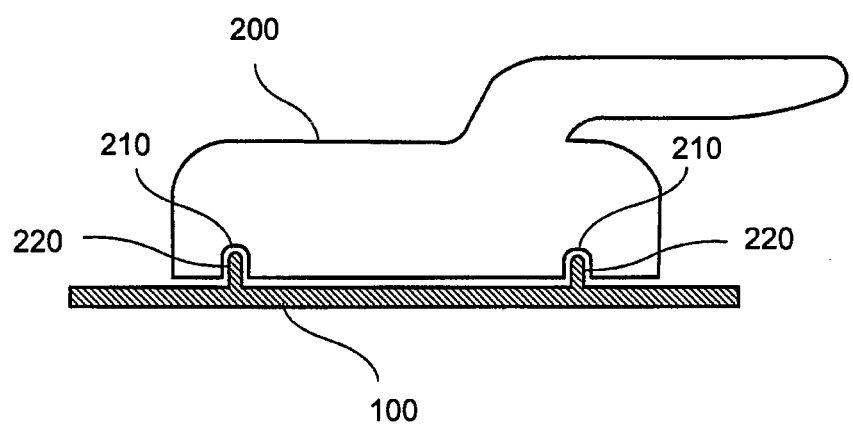
F I G. 1B

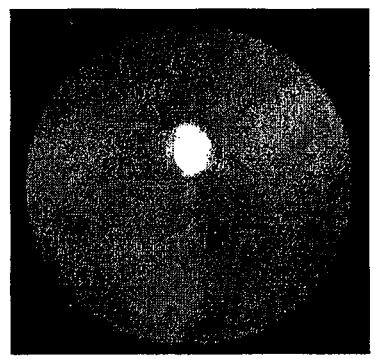
F I G. 2A
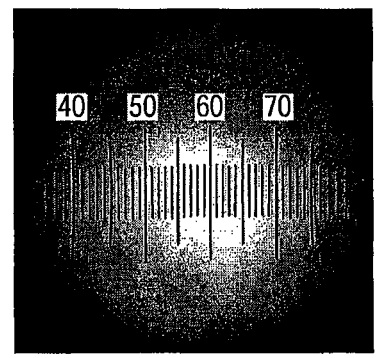
F I G. 2B
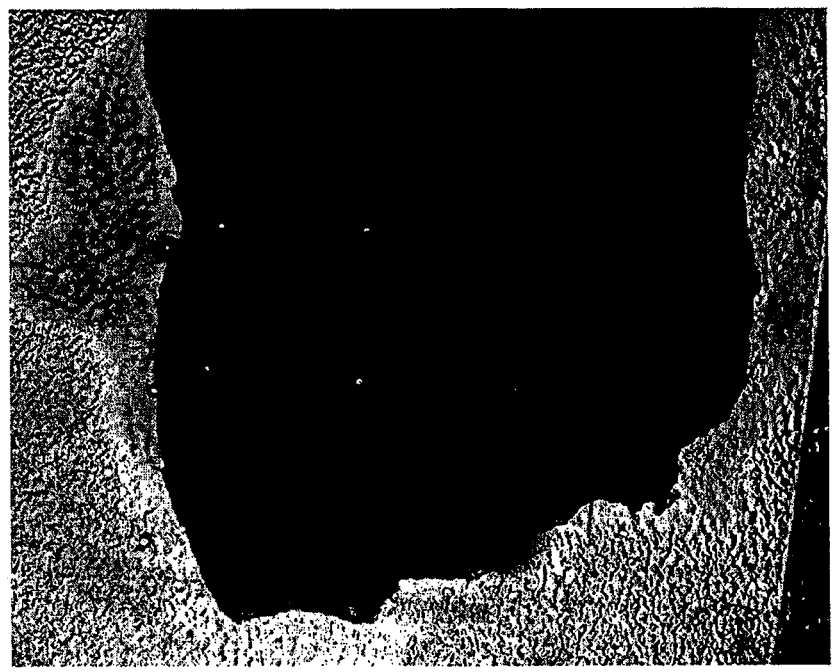
F I G. 3

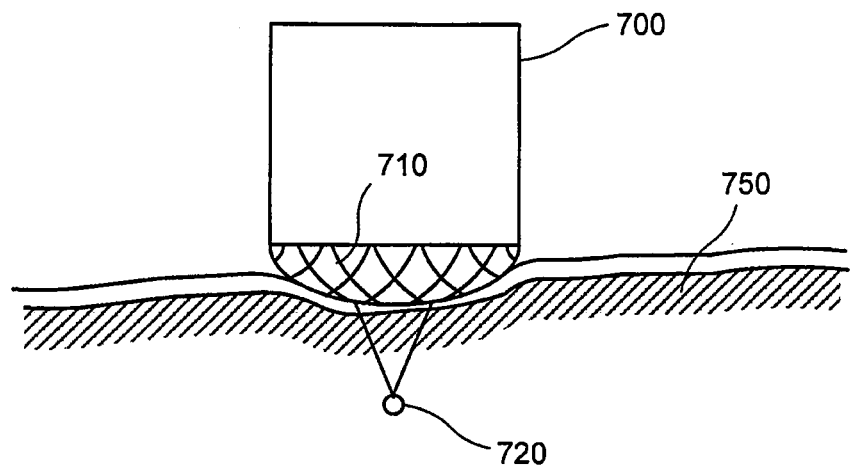
F I G. 7A
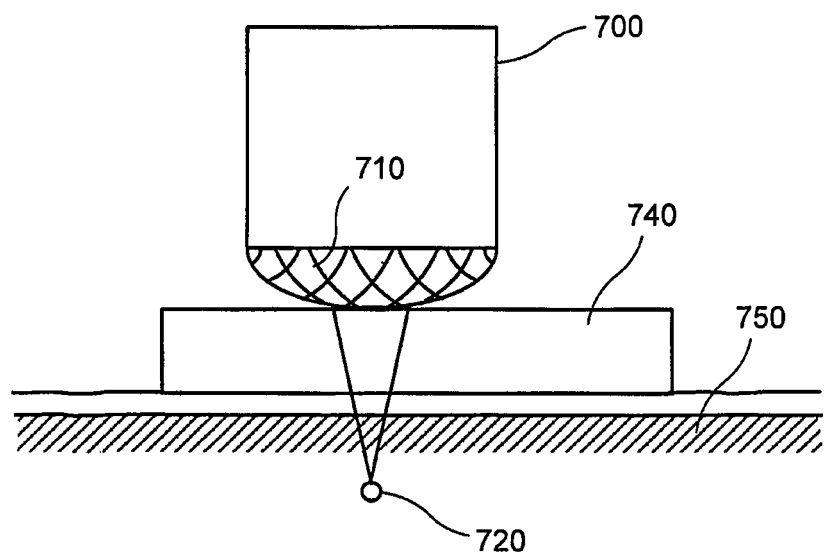
F I G. 7B

METHOD AND APPARATUS FOR SKIN STABILIZATION AND POSITIONING

CROSS-REFERENCE TO RELATED APPLICATION(S)

This application is a continuation of U.S. patent application Ser. No. 12/910,646 filed Oct. 22, 2010, now abandoned, which claims priority to U.S. Provisional Patent Application Ser. No. 61/254,061, filed on Oct. 22, 2009, which are incorporated by reference herein in their entireties.

FIELD OF THE DISCLOSURE

The present disclosure relates to methods, devices and apparatus for stabilizing the surface of skin or other tissue and, more particularly to exemplary embodiments of method, devices and apparatus which can utilize a material film adhered or affixed to at least a portion of the tissue surface to facilitate formation, preservation and/or positioning of one or more small holes formed in the tissue.

BACKGROUND INFORMATION

There is an increasing demand for treating skin defects for both cosmetic and therapeutic reasons. Such defects may be induced by aging, sun exposure, dermatological diseases, traumatic effects, and the like. Certain treatments include penetration of the skin surface to access skin tissue below the surface.

For example, U.S. Patent Publication No. 2007/0239236, which is incorporated by reference herein in its entirety, describes method and apparatus for ablating small holes into tissue using a laser, and then applying a further beam of electromagnetic energy into the hole that is formed in the tissue. The further energy beam can directly irradiate tissue deeper in the skin without passing through or being absorbed by overlying tissue by propagating through the hole.

When using such apparatus or performing such technique, the further beam can be directed into the ablated hole soon after the hole is formed. The hole may tend to reduce in size after it is formed based on the pliability of the surrounding skin tissue and the small size of the hole. Accordingly, it may be desirable to form small ablated holes in skin or other tissue where such holes can be maintained in an open configuration (e.g., prevented from collapsing or closing up) for a longer duration, e.g., on the order of about a second or longer.

Another technique for accessing tissue below a surface includes penetration of the tissue by one or more needles. For example, U.S. Patent Publication Nos. 2005/0222565 and 2008/0082090, which are incorporated by reference herein in their entireties, describe methods and apparatus for delivering electromagnetic energy, e.g., radiofrequency (RF) energy and/or optical energy, to regions of skin tissue below the surface using a plurality of needles. The needles can be provided as an array of needles affixed to a substrate. The needles can be used as electrodes to deliver radiofrequency (RF) energy to proximal tissue regions. Alternatively or additionally, certain needles may include an optical fiber or the like that can deliver optical energy to portions of the tissue proximal to the needle tips.

One limitation of such needles or needle arrays is that the needles may be thin to facilitate insertion into the tissue, reduce the amount of pain or trauma resulting from the insertion, etc. Such consideration can be important when a large number of needles in an array are inserted into tissue substantially at the same time. However, such needles may deform or break when inserted into the tissue, e.g., arising from a lack of sufficient mechanical strength or stability of very fine needles.

One approach to inserting a plurality of thin needles into tissue can include 'drilling' a plurality of small holes using an ablative laser or the like, and then inserting the needles into the ablated holes. Such needles can be small because they do not need to pierce and penetrate the tissue, and therefore may be less strong and/or less rigid than conventional needles configured to penetrate tissue directly. However, such small holes may tend to close up or collapse some time after being formed, as described above. Further, it may be difficult to reliably align a plurality of needles with the plurality of small holes thus formed.

Forming small holes in skin or other tissue can also increase the permeability of the tissue, and may facilitate introduction of various substances into the tissue through the holes or allow fluids present within the tissue to drain out of such holes. In such procedures, it may be desirable to stabilize the holes or openings in the tissue thus formed to delay or prevent their collapse and maintain the permeability and access to deeper portions of the tissue provided by such holes for a longer time.

Therefore, there may be a need to provide method, device and/or apparatus that can facilitate a stabilization of small holes formed in tissue such as skin tissue. Such holes can be formed, e.g., by ablative or mechanical procedures.

SUMMARY OF EXEMPLARY EMBODIMENTS

The present disclosure relates to and describes exemplary embodiments of methods, devices and apparatus for stabilizing a tissue that includes a film at least partially adhered to a surface of the tissue. For example, the film can be formed from a plastic, a polymer, a firmed foam, gel, or liquid, or any other material that can increase mechanical stability of the tissue. In addition and/or alternatively, the film can be formed, e.g., from a material plate or the like, and can be adhered to the tissue using any of a variety of glues, cements, tapes, or the like. The film can also be formed by applying a curable material, e.g., a cement or polymer, to the tissue surface. Such applied film may be directly adherent to the tissue surface without application of a separate adhesive substance.

According to one exemplary embodiment, the tissue underlying the film can be stretched or otherwise placed in a state of tension prior to applying or forming the stabilizing film thereupon. This tension can provide further mechanical stability and/or rigidity to the tissue surface. Further, one or more holes may be formed in the surface-stabilized tissue, and optionally provided or formed through the film, for any one of several reasons, and such holes in the tissue may tend to shrink, collapse, and/or heal more rapidly upon removal of the stabilizing film.

In another exemplary embodiment of the present disclosure, the film can be provided with a first positioning arrangement that may include one or more recesses, protrusions, magnetic elements, or the like. One or more devices may also be provided with a second positioning arrangement configured to interact with the first positioning arrangement provided on the film to facilitate a particular alignment of the one or more devices with the film and/or underlying tissue. For example, a first device can be aligned with the film using the first positioning arrangement and the second positioning arrangement to form one or more holes in the underlying tissue. The first device can be adapted to form such holes, e.g., using a mechanical apparatus such as a needle, or using energy, e.g., an ablative laser or the like. The first device can also be placed at one or more further alignments with respect to the film and the underlying tissue based on the symmetry and/or geometrical configuration of the first and second positioning arrangements. A second device that includes a corresponding or compatible positioning arrangement, e.g., one that is similar to the second positioning arrangement, can then be aligned with the film to introduce energy, e.g., a directed beam of optical energy, and/or an object such as a probe or energy waveguide, into the one or more holes formed in the tissue.

According to an exemplary embodiment of the present disclosure, the first positioning arrangement can include a recess, a protrusion, a groove, a track, a ridge, a magnetic element, and/or a visual marker. The second positioning arrangement provided on the first and/or second device can be configured to interact with the first positioning arrangement to orient the first and/or second device relative to the film and/or the underlying tissue.

In further exemplary embodiments of the present disclosure, the first positioning arrangement provided on the film can include a first guide, e.g., a ridge, groove, track, or the like. The second positioning arrangement provided on the first and/or second device can include a corresponding second guide, e.g., groove, ridge, track, etc. configured to interact with the first guide such that motion of the device over the film is constrained to follow a particular path when the first and second guides interact, e.g., are brought into contact or proximity with one another.

According to an exemplary embodiment of the present disclosure, the first guide can be provided with one or more markers at particular locations on the guide, Such markers can include bumps, notches, magnetic elements, pigmented markings, or the like. The first and/or second device can be provided with a sensor configured to detect the one or more markers. The sensor can optionally be provided in communication with a control arrangement of the first and/or second device that can be configured to control certain aspects of the device. The exemplary film that includes a first guide and one or more markers can be adhered to the tissue surface such that the one or more markers are located at particular locations relative to the tissue. The second guide can be configured to constrain motion of the first and/or second device over the film and underlying tissue, and the sensor can be configured to control a particular aspect of the device when a marker is detected, e.g., over a particular location over the tissue.

In another exemplary embodiment of the present disclosure, a tissue stabilizing film may be provided that can facilitate precise location of a focal point of an optical or ultrasound device within a tissue. The stabilizing film can be adhered to a surface of the tissue, and is preferably sufficiently rigid to inhibit or prevent deformation of the tissue proximal to the stabilizing film when a device, e.g. a laser handpiece, an ultrasound handpiece, or the like, is provided in contact with the stabilizing film. The size and/or shape of the stabilizing film may be selected based on the characteristics of the region of tissue to be treated and the device being used to treat the tissue. The stabilizing film is preferably formed using a material that facilitates transmission or propagation therethrough of energy directed into the tissue by the device. For example, the film can be made using a material that is substantially optically transparent to light energy having a particular wavelength produced by a laser handpiece. In a further exemplary embodiment, the stabilizing film can be formed using a material that is ablatable by such energy provided by the device, e.g., such that a hole in the film can be formed by the energy and the energy then passes through the hole and into the tissue.

An exemplary embodiment of the present disclosure can provide a method for positioning an apparatus relative to a location of a tissue. The exemplary method can include providing a substantially rigid film over an area of tissue to be treated. The film can include a first positioning arrangement that facilitates an engagement of the apparatus in a particular position relative to the film. The exemplary method can further include affixing a portion of the film to a portion of a surface of the tissue, and positioning the apparatus relative to the particular position of the film, and thereby relative to the location of the tissue, using the positioning arrangement.

According to an exemplary embodiment of the method, the film can include a plastic and/or a polymer. The application procedure can be performed using a surgical glue, a cyanoacrylate compound, a cement, a glue, an epoxy, and/or a curable polymer. The exemplary method can further include generating an effect in the tissue at the location using the apparatus. According to the exemplary method, the generation of the effect can include generating thermal damage and/or ablating a hole in the tissue.

Another exemplary embodiment of the method can further include generating a further effect in the tissue at the location. According to the exemplary method, the generation of the further effect can include positioning a further apparatus at a location that can be substantially the same as the location via an engagement of a further feature with respect to the feature to generate the further effect at the location. According to the exemplary method, the generation of the effect can include forming a hole in the tissue, e.g., by ablating tissue, and the generation of the further effect can include directing energy into the hole. According to another exemplary embodiment of the method, the generation of the effect can include forming a hole in the tissue, and the generation of the further effect can include inserting an object at least partially into the hole, where the object can be a probe, a waveguide, a sensor, a needle, and/or an optical fiber.

According to another exemplary embodiment, the method can further include stretching the tissue surface in at least one direction before applying a portion of the film to the tissue surface.

An exemplary embodiment of the present disclosure can provide an apparatus configured to be positioned on at least one particular location of a tissue. The exemplary apparatus can include a second positioning arrangement that can be structured and/or configured to couple or connect to a first positioning arrangement associated with a film configured to be engaged with a portion of a surface of the tissue at the location. The film can be engaged with the surface of the tissue, e.g., using a surgical glue, a cyanoacrylate compound, a cement, a glue, an epoxy, a curable polymer, or the like. The first positioning arrangement and the second positioning arrangement can be configured to engage each other so as to position the device at the particular location. The exemplary apparatus can be further configured to generate an effect in the tissue at or proximal to the at least one location.

In further exemplary embodiments, the apparatus can further include a device configured to generate a further effect at the location. The device can include a third positioning arrangement configured to engage the first positioning arrangement associated with the film such that the device can be positioned at a location substantially the same as the location via an engagement of the first and third positioning arrangements, such that the further effect can be generated at the location. The effect can include drilling or ablating one or more hole(s) in the tissue, and the further effect can include directing energy at least partially into the hole(s). According to another exemplary embodiment of the apparatus, the effect can include drilling and/or ablating one or more hole(s) in the tissue, and the further effect can include inserting one or more object(s) at least partially into the hole(s). The object(s) can include, e.g., a probe, a waveguide, a sensor, a needle, and/or an optical fiber.

An exemplary embodiment of the present disclosure can provide a film for positioning a device on a location of a tissue. The exemplary film can include a portion which includes a first feature which can be structured and/or configured to couple or connect to a second feature of the device. According to the exemplary film, the portion can be configured to engage with a portion of a surface of the tissue at location, and position the device thereon These and other objects, features and advantages of the present disclosure will become apparent upon reading the following detailed description of exemplary embodiments of the disclosure.

BRIEF DESCRIPTION OF THE DRAWINGS

Further objects, features and advantages of the present disclosure will become apparent from the following detailed description taken in conjunction with the accompanying figures showing illustrative embodiments, results and/or features of the present disclosure, in which:

FIG. 1A is a cross-sectional side view of an exemplary film that may be used to stabilize a tissue surface according to an exemplary embodiment of the present disclosure;

FIG. 1B is a cross-sectional side view of a stabilizing film and an apparatus configured to align with the film according to an exemplary embodiment of the present disclosure;

FIG. 2A is an exemplary image of a hole formed in a stabilized tissue which utilized the exemplary embodiment of the film and procedure according to the present disclosure;

FIG. 2B is a further image of the hole shown in FIG. 2A together with size markers which utilized a further exemplary embodiment of the film and procedure according to the present disclosure;

FIG. 3 is an exemplary image of a pattern of 9 holes formed in the tissue which utilized the exemplary embodiment of the film and procedure according to the present disclosure;

FIG. 7A is a cross-sectional side view of an exemplary device configured to provide focused energy into a tissue; and FIG. 7B is a cross-sectional side view of the exemplary device shown in FIG. 7A a being used with a stabilizing film to facilitate a precise depth of the focal point within the tissue according to an exemplary embodiment of the present disclosure.

Figure 4:
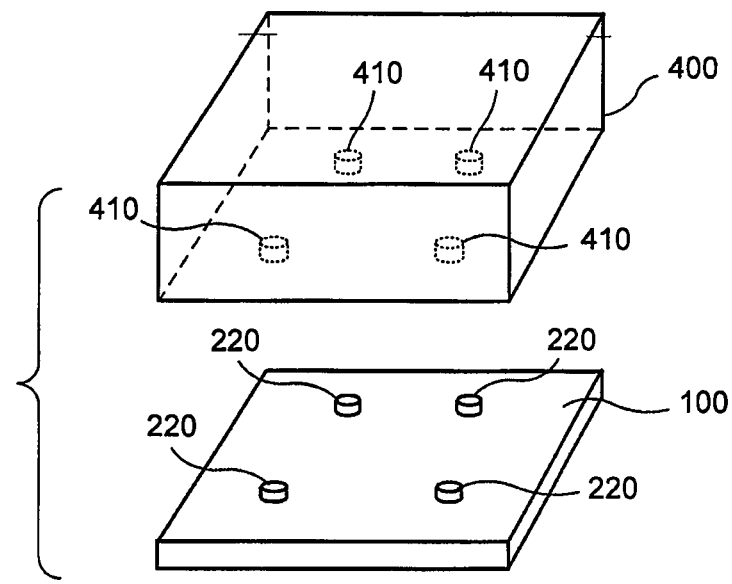
FIG. 4 is a perspective view of a stabilizing film having positioning arrangements and a device having corresponding positioning arrangements according to yet another exemplary embodiment of the present disclosure.

While the present disclosure will now be described in detail with reference to the figures, it is done so in connection with the illustrative embodiments and is not limited by the particular embodiments illustrated in the figures. It is intended that changes and modifications can be made to the described embodiments without departing from the true scope and spirit of the present disclosure.

DETAILED DESCRIPTION OF EXEMPLARY EMBODIMENTS

FIG. 1A shows a cross-sectional illustration of a plurality of holes 150 or channels formed in skin tissue. The holes 150 are shown extending through the epidermis layer 120 and the dermis layer 130, and into the subcutaneous fat layer 140. Shallow holes 150 can also be formed, e.g., holes that extend to one or more depths within the dermis. Such holes 150 may be formed using various techniques. For example, the holes 150 may be ablated using an energy source such as an ablative laser, e.g., a $CO_2$ laser or the like. The holes 150 can also be formed using mechanical procedures, such as inserting needles or shafts into the tissue, or by using other conventional energy sources.

In general, the holes 150 can have a small diameter or width, such that they do not cause substantial disruption of the tissue or leave visible markings on the tissue surface. For example, the width of the holes 150 may be less than about 1 mm, or less than about 0.5 mm. Larger holes can be formed in certain tissues for particular applications.

FIG. 1A illustrates a film 100 that is provided on the surface of the skin. This film 100 can be adhered to the tissue surface in various ways, such as those described below, and may stabilize the upper portions of the holes formed in the tissue. The film 100 can be formed using a variety of materials. For example, the film 100 can be a plastic, a polymer, a metal foil, a firmed foam, gel, or liquid, etc. For example, the film 100 can be formed using poly(methyl) methacrylate (PMMA) or another similar material. The film 100 may be transparent or translucent to facilitate visualization of the underlying tissue and/or accurate location of the holes 150 being formed with respect to particular features of the tissue. For example, the film 100 can be placed over features of the tissue such as a vascular legion (e.g., hemangioma), a tattoo, scar tissue, pigmentation, a mark introduced by person administering the treatment, or the like. Alternatively, the film 100 can be opaque, tinted (to varying degrees), or colored so that the film 100 could facilitate absorption of undesirable radiation. For example, the tint, coloring, and/or opaqueness of the film 100 can be specified to absorb certain frequencies of radiation while allowing other frequencies to pass through the film 100.

The film 100 can be placed on the tissue surface before forming the holes 150. Accordingly, the film material may be selected to be easily ablated or mechanically punctured to facilitate forming of holes 150 that pass through the film 100 and into the underlying tissue. If the holes 150 are formed by ablation, the film 100 material may preferably not contain any materials that can produce substances harmful to the tissue when ablated.

The thickness of the film 100 can be selected to achieve desirable properties based on the particular application. For example, thicker films of a given material may tend to be more rigid and mechanically stable. However, such thicker films may be more difficult to ablate or puncture. The film 100 can be less than about 1 mm thick, or less than about 0.5 mm thick. Such thicknesses can provide sufficient mechanical stabilization to the tissue surface while also facilitating formation of holes therethrough without application of large amounts of energy or force. Other thicknesses may be used, and a particular film thickness can be based on such factors as the film material, the ease of puncturing or ablation, the intended use of the film, etc.

The exemplary film 100 shown in FIG. 1A may be adhered or affixed to the skin surface using a layer of adhesive. Such adhesive can be applied to the tissue surface and/or the film before the film is placed on the tissue. The adhesive can be provided, e.g., as a two-sided sticky tape or the like, which may be initially adhered to either the tissue surface or the film before applying the film to the surface. Alternatively, one side of the film can be provided with an adhesive coating. For example, the film 100 can be provided as a sticky tape or plate that includes an adhesive material provided over at least a portion of one side. In certain embodiments, the adhesive material or coating may be provided on discrete or discontinuous portions of the film 100, rather than over the entire surface thereof.

The adhesive can be any one of a variety of conventional glues or cements, such as a surgical glue, or a combination thereof. For example, the adhesive can be a cyanoacrylate-based adhesive material, such as, e.g., 2-octyl cyanoacrylate, other acrylic adhesives, silicone adhesives, polyurethane adhesives, an epoxy, a curable adhesive, a cement, a glue, or the like. Any of a variety of biocompatible adhesives may also be used with embodiments of the disclosure described herein.

In further exemplary embodiments of the present disclosure, the film 100 can be formed using a curable material, such as a polymer, a resin, an adhesive (e.g., a cyanoacrylate-based adhesive material), or the like. The curable material can be applied in one or more layers on the tissue surface. Preferably, such materials may adhere to the tissue surface and will not cause an adverse reaction with the tissue. Such curable materials can be provided in a sufficient thickness to stabilize the tissue surface as desired for a particular application.

Exemplary embodiments of the present disclosure can also provide and/or maintain the tissue surface (e.g., a skin surface) in a state of tension prior to, during and/or after ablation of the small holes as described herein. For example, the region of tissue surface being stabilized can be stretched or pulled laterally (e.g., in a direction substantially parallel to the local tissue surface) in one or more directions (e.g., unidirectionally or bidirectionally) before or during application of an adhering the film 100 to the tissue surface. The tension can be maintained by the adherence of the mechanically stiff or rigid film to portions of the tissue surface, which can inhibit or prevent relaxation of the stretched tissue to an unstretched state.

Stabilizing a tissue surface under tension can provide several benefits. Such tension can provide further mechanical stability and rigidity to the tissue surface by 'tightening' it. It can also facilitate to delay or prevent closure or collapse of ablated holes, particularly in portions of the tissue close to the surface that may also be under some degree of tension. Further, such applied tension can also facilitate a subsequent closure or reduction in the effective size of such holes 150 after the tension is relaxed, e.g., by removing the stabilizing film from the tissue surface. In this manner, larger holes can be ablated or mechanically formed through a stabilizing film and into stretched tissue, and the initial size of such holes can be reduced after the film is removed and the tension relieved.

For example, various procedures can be performed using such larger holes (e.g., up to about 0.5 mm or 1 mm or more in diameter) formed through a stabilizing film as described herein. After removing the film and allowing the tissue to relax, such larger holes can have a smaller resultant size at the tissue surface, and may not be readily visible under typical viewing conditions. Such a procedure can be used, for example, to facilitate drainage of a lymphatic edema by drilling or ablating one or more holes through a stabilizing film. The film 100 can facilitate maintenance of an open hole between the edema and the tissue surface, allowing a longer drainage time while delaying a spontaneous closing or collapse of the hole.

The exemplary embodiments of stabilization methods and apparatus according to the present disclosure as described herein can be used for several types of procedures. For example, one or more small holes can be formed through a stabilizing film 100 and into skin tissue to a particular depth, as shown in FIG. 1A. The small hole can extend into the tissue to a depth corresponding to a particular target region. Some of the exemplary holes 150 shown in FIG. 1A extend through the epidermal layer 120 of the skin and into the dermis 130 to various depths, whereas other holes are shown to extend through the entire dermis 130 and into the subcutaneous fat layer 140. Shallower holes can also be formed, e.g., holes that extend to a particular depth within the dermal layer 130. Holes can also be formed in other tissues through stabilizing films provided thereupon. For example, holes can be formed in muscle tissue, scar tissue, hair follicles, vascular tissue, organ tissue, ophthalmic tissue, and the like.

After a hole is formed in the tissue to a desired depth, a second beam of energy can be directed into the hole 150. The second beam can be configured to pass substantially through the hole, such that it irradiates a lower portion and/or lateral portions of the hole. Accordingly, energy can be directed onto such subsurface tissues without being absorbed or scattered by overlying tissue to a substantial degree. Applying, adhering or affixing a film to the tissue surface as described herein can stabilize the holes thus formed to provide an extended time in which the second beam (and further beams, if desired, and/or other treatments) can be applied to the holes 150.

For example, tissue regions below the surface can be effectively irradiated with electromagnetic energy having shorter wavelengths (e.g., towards the blue or ultraviolet portions of the spectrum). In conventional, noninvasive irradiation techniques, such radiation would tend to be highly absorbed or scattered by tissue near the surface, and may not penetrate to a sufficient depth to irradiate an underlying target region with a sufficient intensity. An electromagnetic energy having longer wavelengths can also be used to irradiate deeper tissues using the methods and apparatus described herein. Directing the second beam substantially through the ablated hole can increase the fluence applied to the underlying target region while reducing the amount of absorption or scattering by tissue overlying the target region.

The characteristics of the second beam of radiation can be selected based on the desired effect of the radiation on the target tissue. The second beam can be applied immediately following or very soon after formation of the holes using an ablative beam, e.g., before deeper portions of the tissue along the hole have time to close or collapse. Such two-beam techniques for irradiating deeper tissue are described, for example, in U.S. Patent Publication No. 2007/0239236.

The exemplary embodiments of the methods, devices and apparatus according to the present disclosure as described herein can also be used to facilitate application and/or absorption of various therapeutic substances in tissue. For example, a stabilizing film can be formed on or adhered to a tissue surface and a plurality of small holes can be formed through the film and into the tissue, as described above. A therapeutic substance can then be applied such that a portion is introduced into the stabilized holes. In this manner, therapeutic substances can more effectively penetrate the tissue surface and reach the underlying tissue regions as compared, e.g., to such substances being applied to an undisturbed tissue surface. The tissue surface can be stretched and stabilized using the film as described herein prior to forming the holes. After applying the therapeutic substance and relieving the tension, e.g., by removing the film, the upper portion of the holes may tend to collapse more rapidly and facilitate trapping of the therapeutic substance below the tissue surface.

A variety of therapeutic substances can be used in this technique. In general, any substance that can produce a physical or biological effect when contacted with the tissue may be used. Examples of such therapeutic substances include, but are not limited to, antibiotics, medications such as acne medications, dyes, anti-inflammatory compounds, etc. The therapeutic substance can have the form of a liquid, lotion, suspension, solution, or the like. It may be applied by rubbing, spraying, or spreading onto the film after holes are formed therethrough, such that a portion of the therapeutic substance will penetrate into the holes formed in the underlying tissue.

In certain embodiments, the film 100 can include a therapeutic substance that can be released into the tissue after holes are formed therein mechanically or energetically. For example the film 100 can be formed of a compound that includes one or more therapeutic substances, or such substances may be impregnated or discontinuously embedded in the film material. In certain exemplary embodiments, the film can include two or more material layers, where one or more layers can include or be formed of a therapeutic substance. Diffusion or other transport of such therapeutic substances into holes may occur after such holes are formed in tissue stabilized by a film that includes such substances. For example, local heating of tissue and/or the film when ablating holes may promote introduction of therapeutic substances from the film into the holes thus formed. Certain therapeutic substances can also be provided as encapsulated liquids or in a gel form within the film, and such substances may be more readily introduced into the tissue through mechanically-formed holes.

In a further exemplary embodiment of the present disclosure, the stabilizing films described herein can be used for reliable and/or repeatable placement of needles or the like into specific locations of the tissue. For example, a stabilizing film can be provided with one or more holes passing therethrough at particular locations on the film. Such holes can be formed in the film prior to or subsequent to adhering or affixing the film to the tissue surface. One or more needles or other shaped objects (e.g., a waveguide such as an optical fiber, a narrow probe, a sensor, a catheter, or the like) can be inserted through the holes and into the underlying tissue. Such objects can be removed and replaced in the same tissue locations at a later time by re-inserting them through the same holes in the stabilizing film.

For example, an apparatus that includes a plurality of needles affixed to a substrate is described in U.S. Patent Publication No. 2008/0082090. The needle array can include radiofrequency (RF) electrodes, needles containing optical fibers or waveguides (optical needles), and/or hollow needles for injecting fluids. A stabilizing film can be provided that includes a plurality of holes in a pattern that corresponds to the arrangement of needles in such an array. The apparatus containing the needle arrays can then be positioned in a predetermined location relative to the tissue surface by inserting the needles through the holes in the film and into the underlying tissue. The apparatus can also be removed and later replaced in the same location within the tissue by repeating this procedure. The locations of the holes in the stabilizing film can also be provided with a visible marker, e.g., a colored outline or the like, to facilitate visual identification of the hole locations.

In a further exemplary embodiment, the exemplary films described herein can be provided with one or more positioning arrangements 210, 220 that facilitate precise placement of a device relative to a particular location on the skin or tissue surface. The exemplary device and/or arrangement can include, for example, a handpiece or delivery head associated with an energy source such as a laser or an intense pulsed light (IPL) source, and/or the like. The exemplary device and/or arrangement can also be a device that includes one or more needles (e.g., a needle array). More generally, the device can be any device that is configured to provide an interaction with the tissue at one or more specific locations. Such interactions may be, e.g., energetic reactions, mechanical interactions such as piercing or cutting the tissue, or the like.

The exemplary positioning arrangements 210, 220 can be provided in any of several forms. For example, one or more first positioning arrangements 220, e.g., protrusions, pins, ridges, magnetic elements, or the like, can be affixed to the film 100 or formed thereon, and may optionally extend upwards from the upper surface of the film 100. The exemplary device and/or arrangement can be provided with corresponding second positioning arrangements 210, e.g., recesses, holes, notches, further magnetic elements, or the like, on a lower surface thereof. An exemplary combination of first positioning arrangements 220 and second positioning arrangements 210 having the form of protrusions and recesses is shown in FIG. 1B. The recesses 210 can be configured to align with and/or fit onto the protrusions 220 provided on the film.

In further exemplary embodiments of the present disclosure, the protrusions 220 can be provided on a surface of the device, and the recesses 210 can be provided in the film 100, or both the device 200 and film can be provided with recesses 210 and the protrusions 220 configured to align with one another. Accordingly, the exemplary combination of the protrusions 220 and the recesses 210 described herein can be provided to allow a precise positioning of the device 200 relative to the film 100 and the tissue beneath it. In further exemplary embodiments, both the first and second positioning arrangements 220, 210 can include magnetic elements arranged to attract one another when they are in close proximity. Such magnetic elements can be used alone or in combination with protrusions, recesses, grooves, ridges, etc. to further facilitate and/or maintain a particular position or alignment between the film 100 and the device 200.

Such positioning arrangements 210, 220, e.g. protrusions and/or recesses, can be provided on a plurality of devices 200, which can facilitate precise positioning of each device 200 over the film 100 and underlying tissue as described herein. In one exemplary embodiment, the film 100 and a first device can be provided with corresponding protrusions and recesses 210, 220 to facilitate a precise alignment between them. The first device can be configured to generate one or more holes in the film and/or underlying tissue using, e.g., a mechanical needle, an ablative laser, or the like. The first device can also be used to produce any desired effect at one or more particular locations of the tissue that is adhered to the stabilizing film.

A second device can be provided with one or more second positioning arrangements 210, e.g., recesses and/or protrusions substantially similar to those that may be provided on the first device, such that the second device can also be positioned precisely with respect to the film 110. The second device can include, for example, one or more waveguides, e.g., optical fibers or the like, which can be located in positions corresponding to holes formed by the first device. The second device can be placed on the film 100, such that the first and second positioning arrangements 220, 210 engage with one another. The waveguides can then be inserted precisely through the holes formed by the first device. Using such procedure and apparatus, one or more waveguides or other components, e.g., thin probes or the like, can be precisely positioned and inserted into preformed holes in tissue. Accordingly, such components can be reliably inserted into tissue even if they do not have sufficient tip sharpness and/or mechanical strength to penetrate the tissue.

In further exemplary embodiments, the second device can be a further source of optical energy, and it may be configured to direct such optical energy into the holes formed by the first device, e.g., to interact with tissue along the walls of and/or below the formed holes. The second device can also be any device configured to achieve a desired effect or placement at the one or more particular locations of the tissue adhered to the stabilizing film 100. In this manner, each of two separate devices can be precisely aligned with a portion of skin or other tissue to be treated, and each device can direct certain effects or placements to specific locations on the tissue that can be the same or different for each device.

In another exemplary embodiment, the positioning arrangements 210, 220 can be used to facilitate two-beam techniques such as those described, for example, in U.S. Patent Publication No. 2007/0239236. Referring now to FIG. 4, a film 100 having first positioning arrangements 220 can be adhered to the skin of a patient undergoing an exemplary two-beam treatment. In one exemplary embodiment, the film 100 can be placed on the skin surface over a targeted treatment area, such as a vascular legion, or a tattoo, etc. Although the positioning arrangements 220 are shown as four protrusions in an exemplary trapezoidal arrangement in FIG. 4, the film 100 can include any number of positioning arrangements 220 of various types (e.g., rails, recesses, pins, magnets, visual markers, etc.) in any orientation (e.g., in symmetric patterns—squares, rectangles, triangles, parallel rails, asymmetric patterns, etc.).

In another exemplary embodiment, the first positioning arrangements 220 can engage with second positioning arrangements 410 associated with one or more devices 400 used to treat biological tissue. The first positioning arrangements 220 and the second positioning arrangements 410 can engage to facilitate alignment and positioning of the devices 400 during the treatment. For example, as shown in FIG. 4, the device 400 can be a first electromagnetic radiation (EMR) source, or a portion of a handpiece associated with an EMR source, where the EMR source may be configured to generate an EMR that can ablate skin tissue. The first EMR source 400 can include corresponding second positioning arrangements 410 that may be complementary in shape, magnetic polarity, orientation, etc. to at least one of the first positioning arrangements 220.

Although the second positioning arrangements 410 are shown as four recesses in a trapezoidal arrangement in FIG. 4, the second positioning arrangements can be of various types (e.g., rails, recesses, pins, magnets, visual markers, etc.) in any orientation (e.g., symmetric shapes—squares, rectangles, triangles, parallel rails, asymmetric shapes, etc.) that are complementary to the positioning arrangements 220 of the film 100. The first EMR source 400 can be coupled with the film 100 prior to delivering an EMR beam, and the recesses 410 can engage with the positioning arrangements 220. This exemplary engagement can facilitate the alignment and positioning of the first EMR source 400 relative to the film 100 and the tissue to be treated. These positioning arrangements 220 and second positioning arrangements 410 can also be positioned to facilitate a precise positioning of the first EMR source 400 relative to the target area for the treatment. In an exemplary embodiment, the EMR source 400 can include, for example, a $CO_2$ laser or an Er:YAG laser, or any device that can ablate or drill a hole into the tissue. The first EMR source 400 can be used to direct a beam to ablate the tissue and form a hole in the tissue.

After a hole 150 has been ablated or drilled in the tissue, a second EMR source can be used to direct a radiation into the hole to treat the tissue at the bottom of the hole. The film 100 can maintain sufficient tension to keep the holes open after the holes have been created by the first EMR source. In an exemplary embodiment, the second EMR source can include second positioning arrangements 410 similar to those associated with the first EMR source 400. Similar to the engagement of the first EMR source 400, the second EMR source can be coupled with the film 100 (e.g., using the positioning arrangements 220) prior to delivering a second beam to treat the tissue in the holes created by the first EMR source 400. As the second EMR source is pressed against the film 100, the second positioning arrangements 410 of the second EMR source can engage with the first positioning arrangements 220 of the film 100. Since the second positioning arrangements of the first and second EMR sources can engage the same first positioning arrangements 220 of the film 100, such exemplary engagement can facilitate and provide that the second EMR source is precisely aligned with the holes or other patterns of affected tissue generated by the first EMR source. This can ensure that the beam generated by the second EMR source is directed into the holes or onto affected regions generated by the first EMR source. Other devices and apparatuses can include similar second positioning arrangements 410 that can engage with one or more of the first positioning arrangements 220 of the film 100 to align the devices with the holes created by the first EMR source and to allow for additional treatments. In further exemplary embodiments, the positioning arrangements 220, 410 can be used to align a second device (e.g., a second EMR source) such that it avoids affecting tissue regions affected by the first EMR source or other device, e.g., the second device can be configured to generate thermal damage or ablate holes at tissue locations that are between the tissue locations affected by the first device.

As indicated above, the corresponding first and second positioning arrangements 220, 410 (e.g., protrusions and recesses) provided in the apparatus 400 and film 100 can be provided in an asymmetric arrangement, for example, such that their locations correspond to vertices of an isosceles triangle, a trapezoid, or the like (see FIG. 4 showing an exemplary trapezoidal arrangement). Such an asymmetric arrangement can facilitate precise alignment of the apparatus and the film at one particular orientation when the first and second positioning arrangements 220, 410 are engaged.

Figure 5:
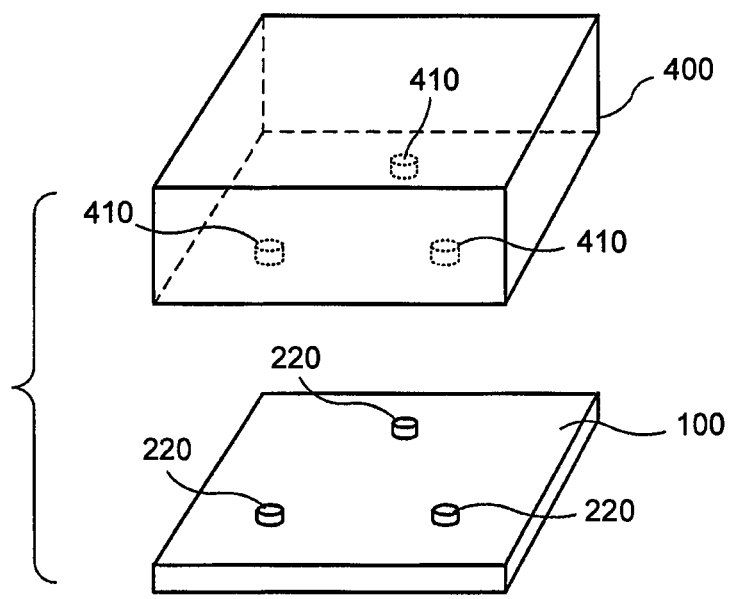
FIG. 5 is a perspective view of a stabilizing film having positioning arrangements and a device having corresponding positioning arrangements according to such exemplary embodiment of the present disclosure.

In a further exemplary embodiment of the present disclosure, patterns or arrangements of first and second positioning arrangements 220, 410 may be provided that exhibit various symmetries. For example, the positioning arrangements 220, 410 may be arranged as an equilateral triangle (as shown in FIG. 5). This exemplary configuration can facilitate positioning of the apparatus in three known positions relative to the tissue and film that are approximately 120 degrees apart in the plane of the film. A fourfold symmetry can be provided using a square arrangement of the corresponding protrusions 220 and recesses 210, such that the exemplary apparatus 400 can be placed at any of four positions with respect to the film and tissue that are 90 degrees apart. A two-fold symmetry can be achieved using a rectangular configuration of the protrusions 220 and recesses 210, and other symmetries (5-fold, 6-fold, etc.) may also be used. For example, such configurations can be used to produce treatments or other effects in multiple locations of the tissue exhibiting the same or similar symmetries as the configuration of the positioning arrangements 220, 410, by applying the apparatus 400 at two or more fixed rotational positions with respect to the film when engaging the positioning arrangements 220, 410.

In a still further exemplary embodiment, the positioning arrangements 220, 410 can include small magnets and/or portions of magnetic material (e.g., iron or the like). Magnets provided on or in certain locations of the stabilizing film can attract further magnets and/or magnetic materials (e.g., ferromagnetic metals or alloys) located in the device that is configured to be placed over the film. 'Matching' of the corresponding magnets and/or magnetic materials can facilitate a particular alignment between the film and the device. In one embodiment, magnets can be provided in both the film and the device, such that the magnets have opposite poles facing each other when the device is in a particular alignment with the film.

Figure 6:
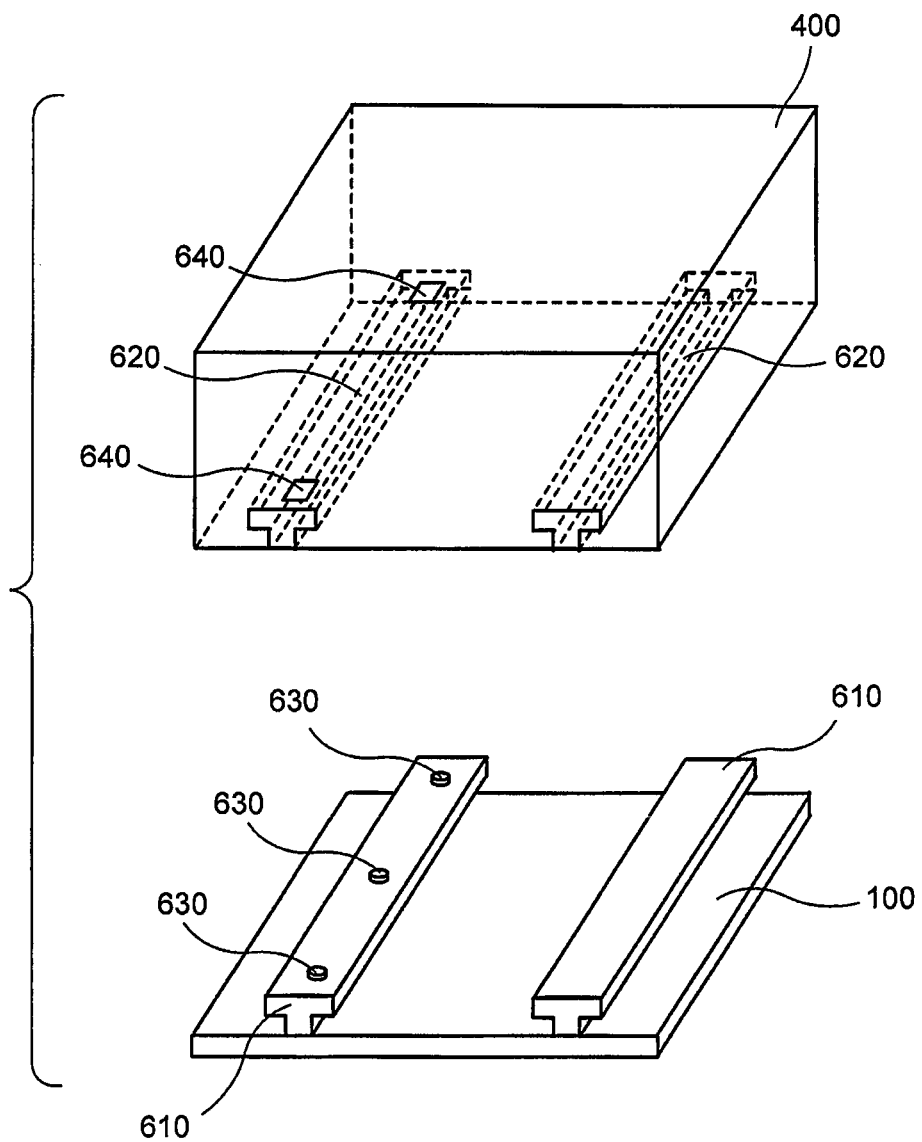
FIG. 6 is a perspective view of a stabilizing film having positioning arrangements and a device having corresponding positioning arrangements according to an exemplary embodiment of the present disclosure.

In a still further exemplary embodiment, the positioning arrangement can include track arrangements 610, 620 that may be provided, e.g., in a form of at least one rail and/or groove (as shown in FIG. 6). A first track arrangement 610 can be provided on the stabilizing film 100 or formed as a part thereof. A device or apparatus 400 designed to engage the first track arrangement 610 of the film 100 can include one or more corresponding second track arrangements 620 configured to slidably engage the first track arrangement 610 of the film 100. The track arrangements 610, 620 can include features such as stoppers that can ensure proper slidable engagement of the device 400 with the film 100.

The exemplary track arrangements 610, 620 shown in FIG. 6 can include lateral protrusions and/or recesses (e.g., protrusions and recesses that can extend at least partially in a lateral direction substantially parallel to the film surface) that can facilitate a positive engagement between the film 100 and the device 400, e.g., such that the device 400 can be translated along first track arrangement 610 but may be prevent from being lifted away from the film 100 while the first and second track arrangements 610, 620 are engaged. In further exemplary embodiments of the present disclosure, the first and second track arrangements 610, 620 can be provided as flat rails and grooves, e.g., that can constrain motion of the device 400 along the direction of the first track arrangement 610 when the device 400 is placed on the film 100 such that the first and second track arrangements 610, 620 are engaged, while allowing the device 400 to be freely lifted away from the film 100.

According to a further exemplary embodiment of the present disclosure, at least one of the first track arrangements 610 can be provided with one or more markers 630 at one or more particular locations thereon. Such markers 630 can include, e.g., bumps, notches, magnetic elements, pigmented markings, or the like provided or formed on the first track arrangement 610 and/or proximal thereto. The first and/or second device can be provided with a sensor 640 configured to detect the one or more markers 630. The exemplary film that includes a first guide and one or more markers can be adhered to the tissue surface such that the one or more markers are located at particular locations relative to the tissue.

The sensor 640 can optionally be provided in communication with a control arrangement associated with the device 400 that can be configured to control certain operational aspects of the device 400. The second track arrangement 620 can be configured to constrain motion of the device 400 over the film 100 and underlying tissue as described herein above, and the sensor 640 can be configured to provide a signal to control a particular aspect of the device 400 when a marker 630 is detected, e.g., when the device 400 is translated over a particular location of the tissue along the first track arrangement 610.

For example, the sensor can include a magnetic detector configured to detect metallic and/or magnetic markers 630. Alternatively, the markers 630 can include indentations or notches provided in the first track arrangements 610, and the sensor 630 can include a conventional microswitch or the like configured to activate when it passes over such notches or indentations. In a further exemplary embodiment of the present disclosure, the markers 630 can be pigmented markings provided on or proximal to the first track arrangements 610, and the sensor 630 can include an optical detector or the like configured to activate when it detects such markings. Other exemplary combinations of suitable markers 630 and sensors 640 configured to detect such markers 630 can also be used with embodiments of the present disclosure. Such exemplary embodiments can provide precise control of the device 400, e.g., including control of operating parameters relative to particular locations in the tissue underlying the film 100 or particular intervals as the device 400 is translated over the film 100 and underlying tissue along a constrained path as described herein.

For example, the sensor 640 can be configured to provide a signal that momentarily provides or cuts off operational power to the device 400, modifies certain properties of an energy provided by the device 400, etc. In one exemplary embodiment of the present disclosure, the device 400 can be configured to generate a pulse of energy directed through the film 100 and into the underlying tissue each time the sensor 640 detects a marker 630 as the device 400 is translated along the first track arrangement 610. Other parameters or operational states of the device 400 can also be controlled based on a detection of the markers 630 by the sensor 640.

In another exemplary embodiment of the present disclosure, a tissue stabilizing film may be provided that can facilitate a precise depth control of a focal point of an optical or ultrasound device (e.g. a laser handpiece, an ultrasound handpiece, or the like) within a tissue. For example, an exemplary EMR device 700 that includes a window 710 configured to contact a surface of a biological tissue 750 is shown in FIG. 7a. The EMR device 700 can be configured to direct a focused spot 720 of electromagnetic radiation into the tissue 750. As illustrated in FIG. 7a, the tissue 750 can deform beneath the window 710 when the EMR device 700 is pressed onto it. This deformation can alter the effective depth of the focal point 720 of the applied energy within the tissue 750 when it is relaxed. The extent of deformation and change in focal point depth can depend on such factors as the size of the window 710, the amount of force used to press the device 700 onto the tissue 750, characteristics of the tissue 750 including any structures therein, etc.

FIG. 7b illustrates an exemplary embodiment of a stabilizing film 740 that can be adhered to a surface of the tissue 750 to facilitate control of the precise depth of the focal point 720 within the tissue 750. The film 740 can be sufficiently rigid to inhibit or prevent deformation of the tissue 750 proximal to the stabilizing film 740 when a device, e.g. a laser handpiece, an ultrasound handpiece, or the like, is provided in contact with the stabilizing film. The film 740 can be adhered or affixed to a surface of the tissue as described herein to further inhibit, reduce and/or prevent the deformation of the tissue 750 beneath the film 740. The size and/or shape of the stabilizing film 740 can be selected based on the characteristics of the region of tissue 750 to be treated and the device being used to treat the tissue.

The exemplary stabilizing film 740 can be formed using a material that facilitates transmission or propagation therethrough of the energy directed into the tissue 750 by the device 700. For example, the film 740 can be made using a material that is substantially optically transparent to light energy having a particular wavelength produced by a laser handpiece. In a further exemplary embodiment of the present disclosure, the stabilizing film 740 can be formed using a material that is ablatable by such energy provided by the device 700. Accordingly, a hole in the stabilizing film 740 can be formed by the energy and the energy can then pass through the hole and into the tissue 750.

The exemplary stabilizing film 740 shown in FIG. 7b can thus facilitate selection and/or maintaining of a precise location of the depth of the focal point 720 below the surface of the tissue 750 as the EMR device 700 or the like is traversed over a surface region of the tissue 750. The stabilizing film 740 can inhibit or prevent deformation of the tissue 750, and provide a fixed distance between the window 710 of the device 700 and the tissue surface. Such stabilization can be enhanced by adhering or affixing the film 740 to the surface of the tissue 750. In contrast, traversing the device 700 directly over the tissue 750 can deform the pliable tissue, and possibly lead to undesirable variations in the effective depth of the focal point 720.

In a still further exemplary embodiment of the present disclosure, the positioning arrangements can include visual markers. The visual markers can include circles, bulls-eyes, X-marks, cross-hairs, etc. that can be aligned with a similar visual marker located on a translucent portion of the device to align the device relative to the film and the tissue to be treated.

In a still further embodiment, the device can include a mechanism to introduce positioning arrangements onto the film. For example, a plain film can be adhered to the skin of a patient, and a device, such as an EMR source, can introduce a positioning arrangement on the film when pressed against the film. This can include printing a visual marker, creating a recess in the film, adhering a protrusion to the film, etc. This can facilitate the device to be located anywhere on the film. Additionally, a second device can engage with the positioning arrangement introduced by the device to ensure that the second device is precisely aligned with the positioning of the first device. This can include the two-beam technique described above, where the first EMR source can introduce a positioning arrangement onto the film, and the second EMR includes corresponding positioning arrangements that can engage the positioning arrangements introduced by the first EMR source.

EXAMPLES

A thin sample of skin tissue having a thickness of about 2 mm was stabilized as described herein by adhering a thin film of PMMA layer (about 300 µm thick) to the tissue surface using ethyl cyanacrylate (KrazyGlue®). A focused 30 W ablative $CO_2$ laser was used to ablate a hole through the film and tissue. The hole was formed using a pulse duration of about 60 ms, corresponding to an applied energy of about 1.8 J. A persistent channel of about 300-400 µm in diameter was formed using this procedure. The hole formed by this exemplary procedure, and a light shining therethrough, are shown in FIGS. 2A and 2B.

An arrangement of 9 holes formed through the exemplary film and tissue described herein are also shown in FIG. 3. The exemplary image in FIG. 3 is shown in transluminescence to improve visibility of the small holes. This image illustrates the ability to form persistent stable and precisely located holes in a tissue using the exemplary methods and apparatus described herein.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

It will thus be appreciated that those skilled in the art will be able to devise numerous systems, arrangements and methods which, although not explicitly shown or described herein, embody the principles of the invention and are thus within the spirit and scope of the present disclosure. In addition, all publications, patents and patent applications referenced herein are incorporated herein by reference in their entireties.

What is claimed is:

1. A system for ablating at least one particular location of a biological tissue, comprising:
    a film configured to engage with at least one portion of a surface of the tissue that includes the at least one particular location; and
    a device comprising a source of ablative electromagnetic radiation,
    wherein the film comprises at least one first feature, and the device comprises at least one second feature,
    wherein at least one portion of the film comprises an ablatable material,
    wherein the at least one first feature is structured or configured to engage with the at least one second feature of the device to position the device over the particular location, such that, in operation, the device ablates a hole in the film over the at least one particular location such that the ablated hole passes through the entire thickness of the film, and further ablates a hole in the tissue at the at least one particular location when the device is activated.

2. The system of claim 1, wherein the film comprises at least one of a plastic or a polymer.

3. The system of claim 1, wherein the source of ablative electromagnetic radiation comprises an ablative laser.

4. The system of claim 1, wherein the film is engaged with the surface of the tissue using at least one of a surgical glue, a cyanoacrylate compound, a cement, a glue, an epoxy, or a curable polymer.

5. The system of claim 1, wherein the at least one first feature comprises a first track arrangement and the at least one second feature comprises a second track arrangement, and wherein the at least one first and second track arrangements are configured to engage one another such that the device is constrained to follow a particular path over the film.

6. The system of claim 5, wherein each of the first and second track arrangements comprises at least one of a guide, a ridge, a groove, or a track.

7. The system of claim 5, further comprising:
at least one marker provided at least one of on or proximal to the at least one first track arrangement; and
at least one sensor associated with the device,
wherein the at least one sensor is configured to detect the at least one marker when the first and second track arrangements are engaged with one another and the device is located at a certain position relative to the film.

8. The system of claim 7, wherein the at least one marker includes at least one of a bump, a notch, a magnetic element, or a pigmented marking.

9. The system of claim 7, wherein the at least one sensor is configured to provide a signal to control an aspect of the device when it detects the at least one marker.

10. A method for affecting a biological tissue at at least one particular location, comprising:
adhering a film comprising an ablatable material to at least one portion of a surface of the tissue that includes the at least one location, wherein the film comprises at least one first feature;
providing a device comprising a source of ablative electromagnetic radiation and at least one second feature,
engaging the at least one first feature with the at least one second feature to position the device at a certain position relative to the at least one particular location; and
activating the device to ablate a hole in the film over the at least one particular location such that the ablated hole passes through the entire thickness of the film, and to further ablate a hole in the tissue at the at least one particular location.

11. The method of claim 10, wherein the at least one first feature comprises a first track arrangement and the at least one second feature comprises a second track arrangement; and further comprising engaging the at least one first and second track arrangements with one another such that the device is constrained to follow a particular path over the film.

12. The method of claim 11, wherein each of the first and second track arrangements comprises at least one of a guide, a ridge, a groove, or a track.

13. The method of claim 11, further comprising:
providing at least one marker provided at least one of on or proximal to the at least one first track arrangement;
providing at least one sensor associated with the device; and
with the at least one sensor, detecting the at least one marker when the first and second track arrangements are engaged with one another and the device is located at a certain position relative to the film.

14. The method of claim 13, wherein the at least one marker includes at least one of a bump, a notch, a magnetic element, or a pigmented marking.

15. The method of claim 13, further comprising, with the at least one sensor, providing a signal to control an aspect of the device when the at least one sensor detects the at least one marker.

* * * * *